United States Patent [19]

Hall et al.

[11] Patent Number: 4,503,258

[45] Date of Patent: Mar. 5, 1985

[54] PROCESS FOR PREPARING 1(4-PENTENOYL)-3,3-DIMETHYLCYCLOHEXANE AND INTERMEDIATES USED IN SAID PROCESS

[75] Inventors: John B. Hall, Rumson; Mark A. Sprecker, Sea Bright, both of N.J.

[73] Assignee: International Flavors & Fragrances Inc., New York, N.Y.

[21] Appl. No.: 551,481

[22] Filed: Nov. 14, 1983

Related U.S. Application Data

[60] Division of Ser. No. 441,221, Nov. 12, 1982, Pat. No. 4,449,007, which is a continuation-in-part of Ser. No. 375,767, May 6, 1982, Pat. No. 4,413,139.

[51] Int. Cl.$^3$ ............................................. C07C 49/21
[52] U.S. Cl. ..................................... 568/376; 568/377
[58] Field of Search ................................ 568/376, 377

[56] References Cited

U.S. PATENT DOCUMENTS

| | | | |
|---|---|---|---|
| 4,081,479 | 3/1978 | Hall et al. | 568/376 |
| 4,081,481 | 3/1978 | Sprecker et al. | 568/376 |
| 4,172,850 | 10/1979 | Trenkle et al. | 568/377 |
| 4,221,687 | 9/1980 | Minagawa et al. | 524/114 |

*Primary Examiner*—James H. Reamer
*Attorney, Agent, or Firm*—Arthur L. Liberman

[57] ABSTRACT

Compounds of the following structure

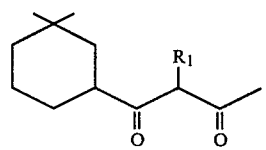

wherein $R_1$ is selected from the group consisting of hydrogen and 2-propenyl are disclosed useful as intermediates in organic synthesis.

3 Claims, 2 Drawing Figures

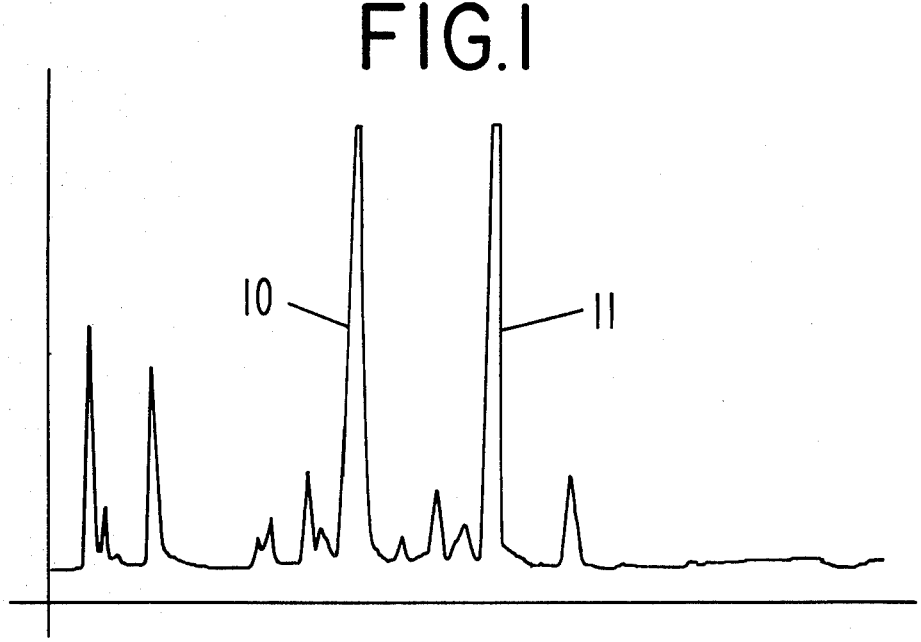
GLC PROFILE FOR EXAMPLE I.
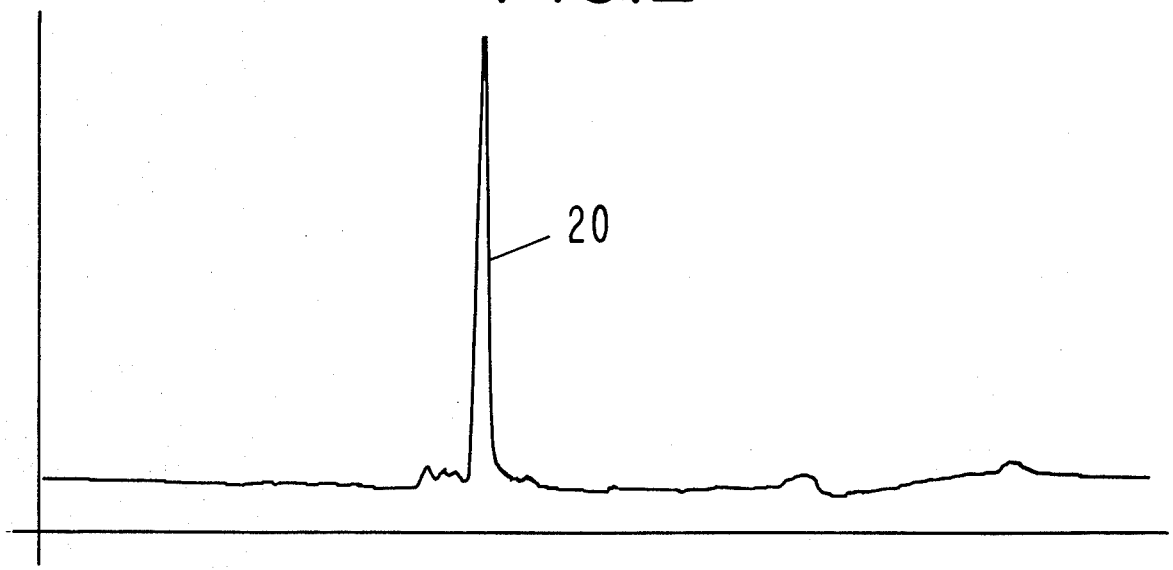
GLC PROFILE FOR EXAMPLE I.

PROCESS FOR PREPARING 1(4-PENTENOYL)-3,3-DIMETHYLCYCLOHEXANE AND INTERMEDIATES USED IN SAID PROCESS

This is a divisional of application Ser. No. 441,221, filed 11/12/82 now U.S. Pat. No. 4,449,007, which, in turn, is a continuation-in-part of Ser. No. 375,767 filed 5/6/82 now U.S. Pat. No. 4,413,139.

BACKGROUND OF THE INVENTION

U.S. Pat. Nos. 4,064,281 issued Dec. 20, 1977 and 4,102,298 issued July 25, 1978 describe processes for preparing compounds defined according to the structure:

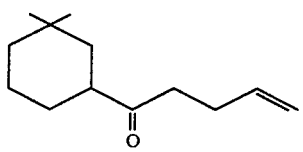

in low yields by reaction of an allylic halide with acetyl-3,3-dimethycyclohexane in the presence of a phase transfer catalyst. Primarily U.S. Pat. No. 4,064,281 teaches the reaction:

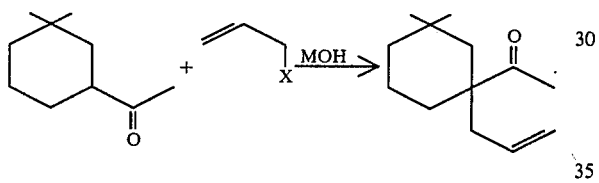

The compound having the structure:

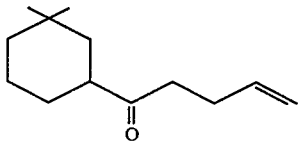

is prepared incidentally to that reaction. Dutch Published application No. 7500838 discloses the preparation of the compound having the structure:

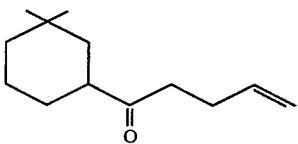

in a manner different in kind from the instant process giving rise to yields far below the yields produced according to the instant process and discloses its use in perfumery and in augmenting foodstuff flavors. The perfumery use of this compound and other members of its class is described as "floral, green, herbaceous and chypre". The use as a galbanum component is also disclosed therein.

Chemical compounds which can provide pineapple-like, oily-sweet, floral, fruity, woody, bark-like and green aroma nuances with minty undertones are highly desirable in the art of perfumery. Many of the natural materials which provide such fragrances and contribute such desired nuances to perfumery compositions and perfumed articles are high in cost, unobtainable at times, vary in quality from one batch to another and/or are generally subject to the usual variations in natural products.

There is, accordingly, a continuing effort to find synthetic materials which will replace, enhance or augment the fragrance notes provided by natural essential oils or compositions thereof. Unfortunately, many of the synthetic materials either have the desired nuances only to a relatively small degree or they contribute undesirable or unwanted odor to the compositions.

BRIEF DESCRIPTION OF THE DRAWINGS

FIG. 1 is the GLC profile for the reaction product of Example I containing the compound having the structure:

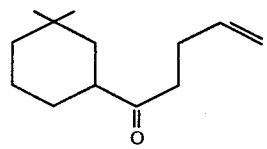

FIG. 2 is the GLC profile of the distillation product of the reaction product of Example I for the compound defined according to the structure:

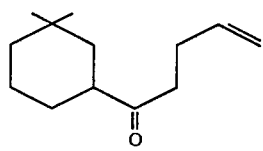

DETAILED DESCRIPTION OF THE DRAWINGS

FIG. 1 is the GLC profile for the reaction product of Example I (conditions: 6 foot×0.25", 12% S.F.96, column programmed at 80°-220° C. at 16° C. per minute). The peak indicated by reference numeral "10" is the peak for the unreacted starting material defined according to the structure:

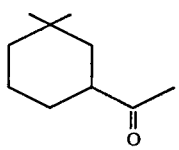

The peak indicated by reference numeral "11" is the peak for the desired product having the structure:

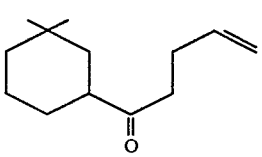

FIG. 2 is the GLC profile for Fraction 18 of the distillation product of the reaction product of Example I containing the compound having the structure:

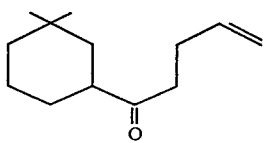

The peak indicated by reference numeral "20" is the peak for the compound having the structure:

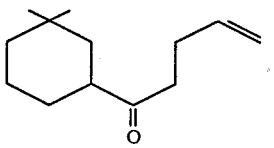

THE INVENTION

Our invention relates to a process for preparing a compound having the structure:

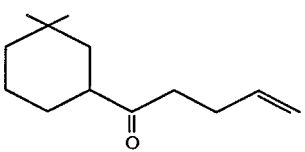

comprising the steps of reacting the compound having the structure:

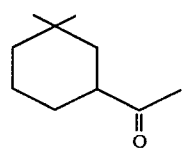

with a lower alkyl acetate having the structure:

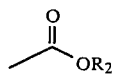

wherein $R_2$ is $C_1$–$C_5$ lower alkyl including methylethyl, n-propyl, i-propyl, n-butyl, 2-butyl, t-butyl and 1-pentyl, 2-pentyl and the like in order to produce a diketone defined according to the structure:

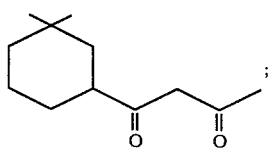

then reacting the resulting diketone with an allyl halide having the structure:

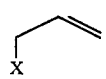

wherein X is bromo or iodo in order to produce a substituted diketone having the structure:

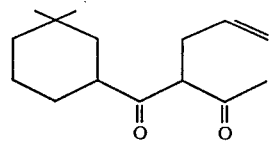

The resulting substituted diketone having the structure:

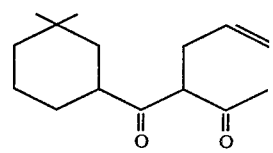

is then reacted with an alkali metal alkoxide by means of a retro-Claisen reaction whereby the compound having the structure:

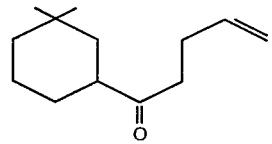

is formed directly.

Our process is embodied in the following reaction scheme:

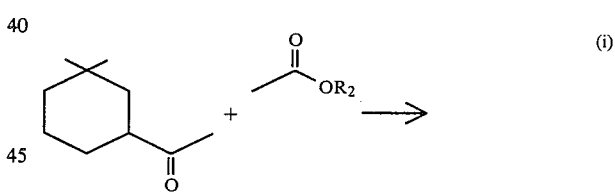
(i)

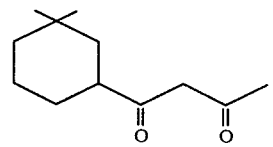

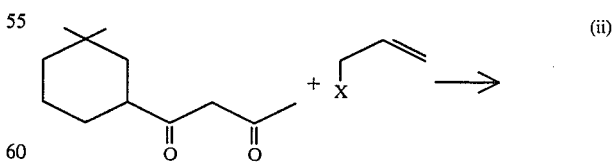
(ii)

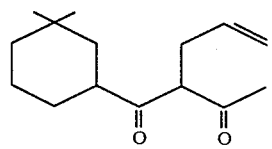

-continued

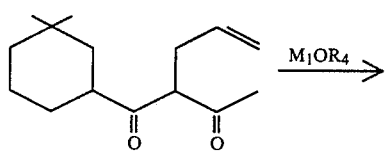 

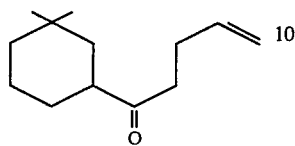

wherein $M_1$ represents alkali metal such as sodium, potassium and lithium and $C_1$–$C_4$ lower alkyl including methylethyl, n-propyl, i-propyl, n-butyl, i-butyl and t-butyl.

Referring to the reaction:

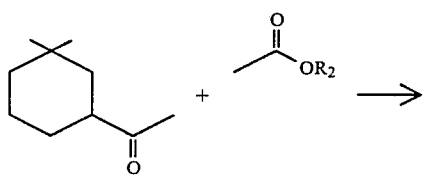

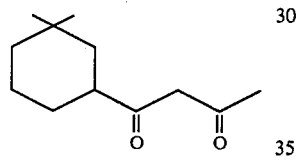

$R_3$ may be $C_1$–$C_5$ lower alkyl including methylethyl, 1-propyl, 2-propyl, 1-butyl, 2-butyl, 1-methyl-2-propyl and 2-methyl-2-propyl. The reaction takes place at a temperature in the range of from about 20° C. up to about 50° C. and a pressure in the range of from about 0.7 atmospheres up to about 5 atmospheres, preferably at a temperature of from about 30° C. up to about 40° C. and at 1 atmosphere pressure. The reaction takes place using an alkali metal alkoxide catalyst such as sodium methoxide, sodium isopropoxide, potassium methoxide and potassium isopropoxide. In addition, aluminum triisopropylate may be used as as catalyst. The mole ratio of compound defined according to the structure:

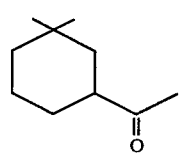

to alkyl acetate is between 1:1 and 1:2 with a preferred mole ratio of a compound having the structure:

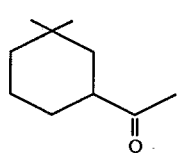

to aklyl acetate of about 1:1.5. The mole ratio of alkali metal alkoxide or aluminum isopropylate to the compound having the structure:

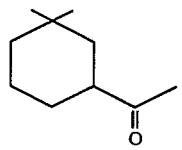

is between 0.5:1 and 1:0.5 with a preferred mole ratio of alkali metal alkoxide or aluminum triisopropylate to the compound having the structure:

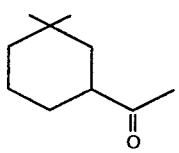

is between 0.5:1 and 1:0.5 with a preferred mole ratio of alkali metal alkoxide or aluminum triisopropylate to the compound having the structure:

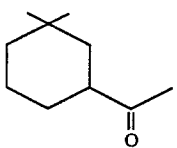

being about 1:1.

The compound having the structure:

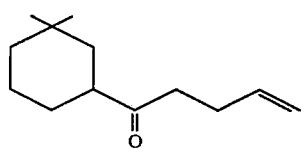

may be isolated and used for its organoleptic properties in augmenting or enhancing the aroma of perfume compositions, colognes or perfumed articles or it may be used in the subsequent reaction (ii) of this sequence.

In carrying out reaction (ii) of the sequence, to wit:

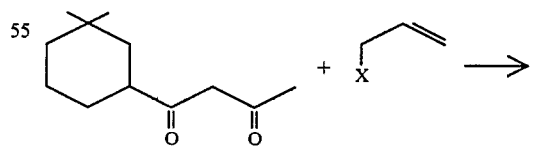

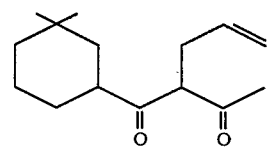

the mole ratio of diketone having the structure:

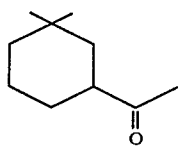

to the allyl halide having the structure:

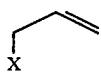

is between 1:1 and 1:2 with a preferred mole ratio of about 1:1. In this reaction the allyl halide having the structure:

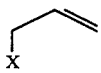

is one wherein X is bromo or iodo. Actually allky chloride can be used as a reactant but the allyl iodide or allyl bromide must be produced in situ. Accordingly, conveniently, allyl chloride may be used along with such materials as sodium iodide or sodium bromide whereby the allyl iodide or allyl bromide is produced in situ.

This reaction takes place at reflux conditions preferably at a temperature in the range of from about 60° up to about 80° C., most conveniently at atmospheric pressure. However, pressures greater than or less than atmospheric pressure may be used. Accordingly, the pressure of reaction may vary from about 0.7 atmospheres up to about 10 atmospheres at reflux conditions. Higher temperatures of reaction give rise to shorter time periods of reaction. For example, when carrying out the reaction at 60°–70° C., the time of reaction is about 8 hours.

At the end of this reaction the reaction mass is purified by means of solvent stripping. The reaction product is then further reacted by means of reaction (iii) to wit:

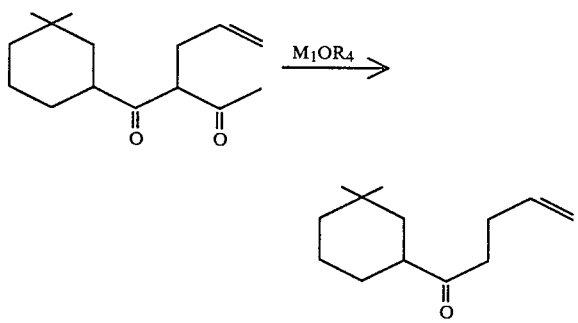

wherein $M_1$ is alkali metal such as sodium, potassium and lithium and $R_4$ is lower alkyl such as methylethyl, 1-propyl, 2-propyl, 1-methyl-2-propyl and 2-methyl,2-propyl. In the alternative, a reaction can take place in the presence of aluminum triisopropylate. The reaction preferably takes place in aqueous solution. In place of the alkali metal alkoxide used or the aluminum triisopropylate used, an aqueous alcoholic alkali metal hydroxide solution can be used. Thus, for example, 1-liter of 50% aqueous sodium hydroxide may be admixed with 500 ml of water and 500 ml methyl alcohol and the resulting mixture is then admixed with the compound having the structure:

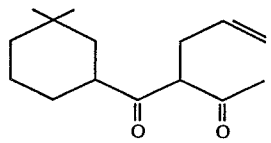

This reaction is carried out at a temperature of between 35° C. and 50° C.

The resulting product is then distilled from the reaction mass by means of fractional distillation.

As an olfactory agent, the diketone of our invention having the structure:

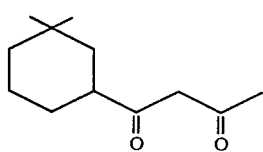

(hereinafter referred to as "the diketone of our invention") can be formulated into or used as a component of a "perfume composition" or can be used as a component of a "perfumed article" or the perfume composition may be added to perfumed articles.

The term "perfume composition" is used herein to mean a mixture of organic compounds including, for example, alcohols, aldehydes, ketones (other than the diketone of our invention), nitriles, ethers, lactones, epoxides, natural essential oils, synthetic essential oils and hydrocarbons which are admixed so that the combined odors of the individual components produce a pleasant or desired fragrance. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation, and substances which retard evaporation and (d) topnotes which are usually low-boiling, fresh-smelling materials.

In perfume compositions, the individual component will contribute its particular olfactory characteristics, but the overall effect of the perfume composition will be the sum of the effects of each of the ingredients and, in certain instances, a synergistic effect as a result of the addition of certain ingredients. Thus, the individual compounds of this invention, or mixtures thereof, can be used to alter the aroma characteristics of a perfume composition, for example, by highlighting or moderating the olfactory reaction contributed by another ingredient in the composition.

The amount of the diketone of our invention which will be effective in perfume compositions depends on many factors, including the other ingredients, their amounts and the effects which are desired. It has been found that perfume compositions containing as little as 0.05% of the diketone of this invention or even less can be used to impart interesting, pineapple-like, oily, sweet, floral, fruity, woody, bark-like and green aromas with minty undertones to soaps, liquid or solid anionic, cationic, nonionic or zwitterionic detergents, cosmetics, cosmetic powders, liquid or solid fabric softeners, drier-added fabric softener articles, (e.g., BOUNCE ®, a registered trademark of the Procter & Gamble Company of Cincinnati, Ohio), optical brightener compositions, hypochlorite bleach compositions, fragranced polymers, hair conditioners and other products. The amount employed can range up to 70% or even higher and will depend on considerations of cost, nature of the end product and the effect desired on the finished product and particular fragrance sought. Thus, for example, when fragrancing liquid bleach compositions containing alkali metal hypochlorite such as, for example, sodium hypochlorite, for example CLOROX ® (registered trademark of Clorox, Inc.), the amount employed can range as high as 100% of the fragrance involved in the liquid bleach. Indeed, a distinctive aspect of our invention is the use of the diketone of our invention in a stable liquid bleach composition.

The diketone of our invention can be used alone or in a perfume composition as an olfactory component in detergents, soaps, space odorants and deodorants; perfumes; colognes, toilet waters; bath salts; hair preparations such as lacquers, brilliantines, pomades and shampoos; cosmetic preparations, such as creams, deodorants, hand lotions, sun screens, powders such as talcs, dusting powders, face powders and the like; liquid bleaches such as sodium hypochlorite-containing bleaches; floor waxes, automobile aromas and automobile polish compositions. When used as an olfactory component of a perfumed article as little as 0.01% of the diketone of our invention will suffice to impart an interesting pineapple-like, oily-sweet, floral, fruity, woody, bark-like and green aroma with minty undertones. Generally no more than 1.5% is required to impart such an aroma. However, in view of the rather low cost of the diketone of our invention up to 100% of the perfume composition can be the diketone itself.

In summary, the range of the diketone of our invention in the perfumed article can be from 0.01% up to 1.5% or even higher.

In addition, the perfume composition can contain a vehicle or carrier for the diketone along with other ingredients. The vehicle can be a liquid such as a non-toxic alcohol such as ethanol, a glycol such as propylene glycol or the like. The carrier can be an adsorbent solid such as a gum (e.g., guar gum or xanthan gum or gum arabic) or components for encapsulating the composition such as gelatin which can be used to form a capsule wall surrounding the perfume oil as by means of coacervation with gelatin or by means of formation of a polymer around the perfume oil as by polymerizing a urea formaldehyde prepolymer.

The following Example I serves to illustrate a method for carrying out the process of our invention and producing intermediates useful in our invention. All parts and percentages given herein are by weight unless otherwise specified.

EXAMPLE I

PREPARATION OF 1(4-PENTENOYL)-3,3-DIMETHYLCYCLOHEXANE

Reaction:

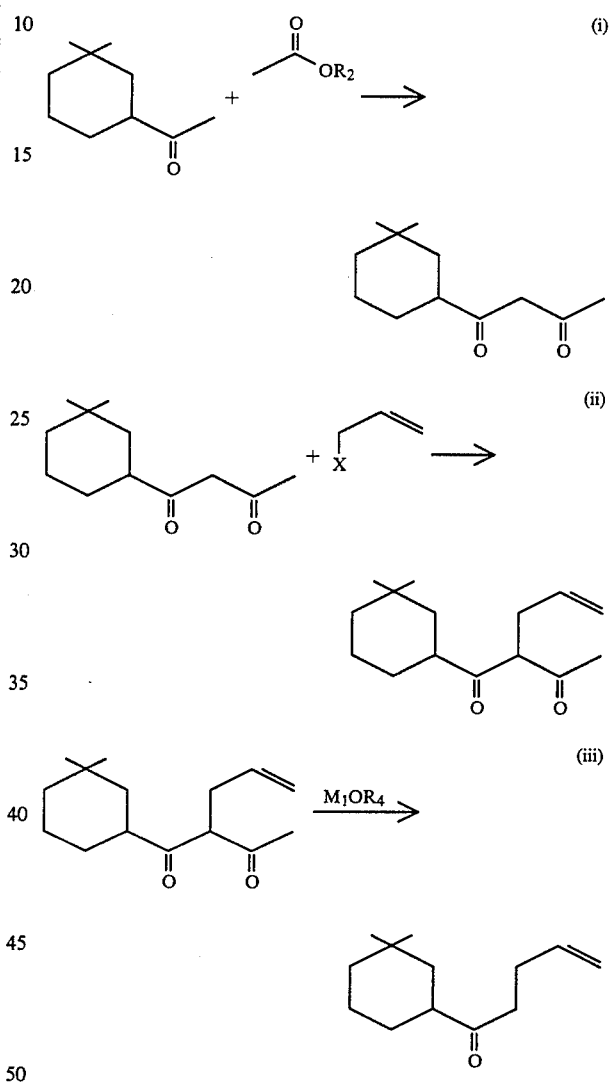

Into a 12-liter reaction flask equipped with stirrer, thermometer, condenser, "Y" tube, addition funnel, cooling bath, heating mantle, nitrogen blanket apparatus and gas bubbler is placed 2940 ml (30 moles) of ethyl acetate, 600 ml isopropyl alcohol, 1080 grams of sodium methoxide (20 moles) and 150 grams (1 mole) of sodium iodide.

The reaction mass is cooled to 31°–32° C. and, over a period of two hours while maintaining the reaction temperature at 30°–32° C., 1540 grams (7.4 moles) of 1-acetyl-3,3-dimethylcyclohexane is added to the reaction mass. After the addition of the 1-acetyl-3,3-dimethylcyclohexane is complete, the reaction mass is stirred for a period of two hours while maintaining the temperature at 27°–31° C.

The compound having the structure:

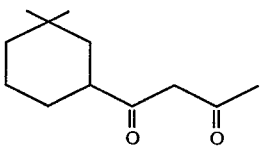

may be isolated and used for its organoleptic properties as stated in Examples II, et seq. Thus, the compound having the structure:

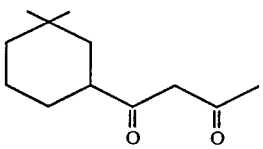

is distilled at 88°-93° C. at 3 mm/Hg pressure yielding a pineapple, oily, sweet, fruity, floral, woody, bark-like, and green aroma bearing material with minty undertones.

Over a period of 15 minutes, 815 ml of allyl chloride is then added to the reaction mass while maintaining the temperature at 30°-35° C. The reaction mass is then refluxed at 60°-65° C. for a period of one hour.

At the end of the one hour period while maintaining the reaction mass at 60°-62° C. an additional 815 ml (10 moles) of allyl chloride is added to the reaction mass. The reaction mass is heated at 60°-62° C. over a period of eight hours.

The entire reaction mass is then transferred by vacuum to a 12-liter separatory flask in a solution of 200 ml glacial acetic acid and 200 ml water is added in order to bring the pH of the reaction mass to 6. The resulting product is then washed with 4-liters of water and the aqueous layer is separated. The organic phase is transferred back to a 12-liter reaction flask which is fitted with a "rushover" head. The contents are stripped at atmospheric pressure to a pot temperature of 100° C. 3-Liters of material is collected.

A solution containing 1-liter of 50 percent sodium hydroxide, 500 ml water and 500 ml methanol is produced.

1-Liter of the resulting alcoholic sodium hydroxide solution is added to the reaction mass at 41° C. (using cooling). The feed of the alcoholic sodium hydroxide solution to the reaction mass is over a 0.75 hour period. The temperature of the reaction mass is permitted to rise to 68° C. 500 Ml additional alcoholic sodium hydroxide solution is then added to the reaction mass.

The contents of the reaction mass are then transferred back to the separatory funnel and the aqueous layer is separated from the organic phase. The organic phase is acidified to a pH of 6 with 50 ml glacial acetic acid and then washed with 500 ml water. The organic phase is then distilled in a 12" Goodloe column yielding the following fractions:

| Fraction No. | Vapor Temp. (°C.) | Liquid Temp. (°C.) | Vacuum mm/Hg. Pressure | Reflux Ratio | Weight of Fraction |
| --- | --- | --- | --- | --- | --- |
| 1 | /56 | /83 | 175.0 | 1:1 | 119.0 |
| 2 | 37 | 123 | 35.0 | 1:1 | 109.3 |
| 3 | 85 | 126 | 30.0 | 1:1 | 70.5 |
| 4 | 67 | 112 | 20.0 | 3:1 | 71.0 |
| 5 | 81 | 104 | 13.0 | 3:1 | 85.4 |

-continued

| Fraction No. | Vapor Temp. (°C.) | Liquid Temp. (°C.) | Vacuum mm/Hg. Pressure | Reflux Ratio | Weight of Fraction |
| --- | --- | --- | --- | --- | --- |
| 6 | 75 | 100 | 9.0 | 3:1 | 83.7 |
| 7 | 74 | 98 | 9.0 | 3:1 | 50.9 |
| 8 | 74 | 100 | 8.5 | 4:1 | 63.2 |
| 9 | 74 | 105 | 8.5 | 4:1 | 79.3 |
| 10 | 76 | 107 | 8.0 | 4:1 | 94.4 |
| 11 | 80 | 112 | 8.0 | 4:1 | 94.5 |
| 12 | 89 | 115 | 8.0 | 4:1 | 95.9 |
| 13 | 90 | 116 | 8.0 | 4:1 | 78.6 |
| 14 | 92 | 117 | 8.0 | 4:1 | 41.7 |
| 15 | 85 | 101 | 2.8 | 4:1 | 42.2 |
| 16 | 90 | 105 | 2.8 | 4:1 | 33.0 |
| 17 | 92 | 110 | 3.0 | 4:1 | 78.9 |
| 18 | 90 | 107 | 2.8 | 4:1 | 83.0 |
| 19 | 90 | 110 | 2.6 | 4:1 | 96.5 |
| 20 | 90 | 112 | 2.5 | 4:1 | 85.5 |
| 21 | 95 | 126 | 7.4 | 4:1 | 105.5 |
| 22 | 105 | 152 | 7.4 | 4:1 | 106.8 |
| 23 | 130 | 195 | 7.4 | 4:1 | 92.8 |
| 24 | 155 | 235 | 2.0 | 4:1 | 58.4 |

FIG. 1 is the GLC profile prior to distillation. (Conditions: 6'×0.25", 12%, S.F.-96, column programmed at 80°-220° C. at 16° C. per minute.) The peak indicated by reference numeral 10 is the peak for the unreacted starting material, the 1-acetyl-3,3-dimethylcyclohexane. The peak indicated by reference numeral "11" is the peak for the reaction product defined according to the structure:

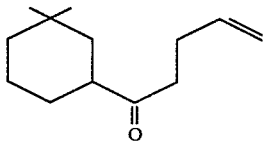

FIG. 2 is the GLC profile for Fraction 18 of the foregoing distillation product containing the compound having the structure:

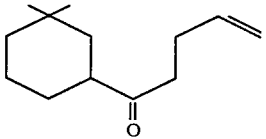

The structure of this compound is confirmed by means of MNR, IR and mass spectral analyses.

EXAMPLE II

SPICY-FLORAL FRAGRANCE

The following spicy-floral fragrance is prepared:

| Ingredients | Parts by Weight |
| --- | --- |
| Coumarin | 6.0 |
| Musk Ambrette | 8.0 |
| Benzyl Salicylate | 12.0 |
| Bergamot Oil | 6.0 |
| Hydroxycitronellal | 5.0 |
| Lavandin Abriolis | 4.0 |
| Patchouli Oil Light | 1.0 |
| Phenyl Ethyl Alcohol | 6.0 |
| Gamma Methyl Ionone | 1.0 |
| Vetivert Oil, Bourbon | 8.0 |
| Benzyl Acetate | 14.0 |
| Linalool | 8.0 |

| Ingredients | Parts by Weight |
| --- | --- |
| Amyl Cinnamic Aldehyde | 10.0 |
| Indole (10% in diethyl phthalate | 1.0 |
| Eugenol | 2.0 |
| The diketone produced according to Example I having the structure: 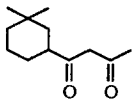 | 8.0 |

The diketone having the structure:

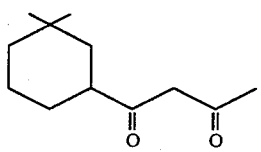

adds to the spicy-floral fragrance an interesting pineapple, oily sweet, fruity, woody, bark-like, green and minty profile of nuances. Thus, the formulation can be described as "spicy and floral with oil sweet, fruity, woody, bark-like, green and minty nuances".

EXAMPLE III

PREPARATION OF A COSMETIC POWDER COMPOSITION

A cosmetic powder is prepared by mixing in a ball mill 100 grams of talcum powder with 0.25 grams of a perfume substance as set forth in Table I below. The resulting powder has an excellent aroma as set forth in Table I below:

TABLE I

| Perfume Substance | Aroma Description |
| --- | --- |
| Diketone produced according to Example I having the structure: 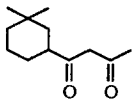 | A pineapple-like, oily sweet, floral, fruity, woody, bark-like and green aroma profile with minty undertones. |
| Perfume composition of Example II | Spicy and floral with oily sweet, fruity, woody, bark-like, green and minty nuances. |

EXAMPLE IV

PERFUME LIQUID DETERGENT

Concentrated liquid detergent (lysine salt of n-dodecylbenzene sulfonic acid as more specifically described in U.S. Pat. No. 3,948,818, issued on Apr. 6, 1976, the specification for which is incorporated herein by reference) with aroma nuances as set forth in Table I of Example III supra are prepared containing 0.10%, 0.15%, 0.20%, 0.25%, 0.30% and 0.35% of the substances as set forth in Table I of Example III supra. They are prepared by adding and homogeneously mixing the appropriate quantity of fragrance formulation of Table I of Example III supra in the liquid detergents. The detergents all possess excellent aromas, the intensity increasing with greater concentration of perfume substance of Table I of Example III.

EXAMPLE V

PREPARATION OF A COLOGNE AND HANDKERCHIEF PERFUME

The perfume substances as set forth in Table I of Example III supra are incorporated into colognes at concentrations of 2.0%, 2.5%, 3.0%, 3.5% 4.0%, 4.5% and 5.0% in 75%, 80%, 85% and 90% aqueous food grade ethanol; and into handkerchief perfumes at concentrations of 15%, 25% and 30% (in 80%, 85%, 90% and 95% aqueous food grade ethanol solutions). Distinctive and definitive aroma nuances as set forth in Table I of Example III are imparted to the colognes and to the handkerchief perfumes at all levels indicated above.

EXAMPLE VI

PREPARATION OF SOAP COMPOSITIONS

One hundred grams of soap chips (IVORY ®, produced by the Procter & Gamble Company of Cincinnati, Ohio) are mixed with 1 gram of each of the perfumery substances of Table I of Example III, supra until homogeneous compositions are obtained. In each of the cases, the homogeneous compositions are heated under 3 atmospheres pressure at 180° C. for a period of three hours and the resulting liquids are placed into soap molds. The resulting soap cakes, on cooling, manifest excellent aromas as set forth in Table I of Example III supra.

EXAMPLE VII

PREPARATION OF SOLID DETERGENT COMPOSITIONS

A detergent is prepared from the following ingredients according to Example I of Canadian Pat. No. 1,007,948, (the specification for which is incorporated herein by reference):

| Ingredient | Percent by Weight |
| --- | --- |
| Neodol ® 45-11 (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is phosphate-free detergent. A total of 100 grams of said detergent is admixed with 0.10, 0.15, 0.20 and 0.25 grams of the substances of Table I of Example III supra. The detergent samples in each case have excellent aromas as set forth in Table I of Example III supra.

EXAMPLE VIII

Utilizing the procedure of Example I at column 15 of U.S. Pat. No. 3,632,396, (the disclosure of which is incorporated by reference herein) a nonwoven cloth substrate useful as a drier-added fabric softening article of manufacture is prepared wherein the substrate, the substrate coating and the outer coating and the perfuming material are as follows:

1. A water dissolvable paper ("Dissolvo Paper");
2. Adogen 448 (melting point about 140° F.) as the substrate coating; and 3. An outer coating having the following formulation (melting point about 150° F.):
57% $C_{20-22}$ HAPS
22% isopropyl alcohol
20% antistatic agent
1% of one of the perfume substances of Table I of Example III, supra.

Fabric softening compositions having aromas as set forth in Table I of Example III are prepared which essentially consist of a substrate having a weight of about 3 grams per 100 square inches; a substrate coating having a weight of about 1.85 grams per 100 grams of substrate; and an outer coating having a weight of about 1.4 grams per 100 square inches of substrate, thereby providing a total aromatized substrate and outer coating weight ratio of about 1:1 by weight of the substrate. The aromas as set forth in Table I of Example III are imparted in a pleasant manner to the head space in the drier on operation thereof using each of the drier-added fabric softening nonwoven fabric samples.

In the following examples, Aromox ® DMC-W and Aromox ® DMMC-W are 30% aqueous solutions of dimethyl cocoamine oxide; and Aromox ® NCMDW is a 40% aqueous solution of N-cocomorpholine oxide produced by Armac Division of ADZO of Chicago, Ill.

EXAMPLE IX

Four drops of one or more of the perfume substances as set forth in Table I of Example III supra is added to 2 grams of Aromox ® DMC-W to produce a clear premix. The clear premix is added to 200 grams of CLOROX ® with stirring resulting in a clear, stable, single phase solution. Sufficient 1M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint, pleasant aroma as set forth in Table I of Example III supra. Furthermore, no such characteristic "hypochlorite" aroma is retained on the hands of the individual handling such laundry in both the wet and the dry states.

EXAMPLE X

Aromox ® DMMC-W in various quantities is mixed with 0.1 grams of each of the substances of Table I of Example III supra. The resulting premixes are then added to 200 grams of an aqueous 5% sodium hypochlorite solution. Sufficient 12.5M aqueous NaOH is added to bring the pH of each of the mixtures up to 13. The following results are obtained:

| Percentage Aromox ® DMMC-W | Clarity of hypochlorite solution after addition of premix |
| --- | --- |
| 0.23% | Clear after three days |
| 0.15% | Clear after three days |
| 0.08% | Initially slightly turbid; two phases exist after three days |

When the 5% aqueous sodium hypochlorite solutions are used as laundry bleaches, the resulting laundry batches on dry-out in an atmosphere of 65% relative humidity yields substantially no characteristic "hypochlorite" odor but do have faint, pleasant aromas as set forth in Table I of Example III supra. Furthermore, no such characteristic "hypochlorite" aroma is retained on the hands of the individual handling such laundry batches in both the wet and the dry states.

EXAMPLE XI

Two grams of Aromox ® DMMC-W are admixed with eight drops of each of the perfume substances of Table I of Example III supra. Each of the premixes is then added with stirring to 200 grams of a 7% aqueous solution of lithium hypochlorite. Sufficient 3M aqueous LiOH is added to bring the pH of the solution to 13.4. The mixtures are then heated to 120° F. and maintained at that temperature with stirring for a period of one week. The resulting solution remains clear in a single phase. When used as laundry bleaches, the resulting bleached laundry batches on dry-out in an atmosphere of 50% relative humidity retain an aroma as described in Table I of Example III whereas without the use of the substances of Table I of Example III, the bleached laundry batches have faint characteristic disagreeable "hypochlorite" aromas.

EXAMPLE XII

Two grams of Aromox ® DMMC-W are admixed with eight drops of each of the substances of Table I of Example III supra. The premixes are then added with stirring to 200 grams of a mixture containing 4.5% aqueous sodium hypochlorite and 4.5% aqueous lithium hypochlorite. Sufficient 4M aqueous LiOH is added to bring the pH of the solutions to 13.4. The mixtures are then heated to 120° F. and maintained at that temperature for a period of one week. The resulting solutions remain clear in a single phase. When used as laundry bleach, the resulting bleached laundry batches on dry-out in an atmosphere of 50% relative humidity retain in aroma as set forth in Table I of Example III supra whereas without the use of the perfume substances as set forth in Table I of Example III supra, the bleached laundry batches have faint characteristic and disagreeable "hypochlorite" aromas.

EXAMPLE XIII

Two grams of Aromox ® DMMC-W are admixed with eight drops of one of the perfume substances of Table I of Example III supra. These premixes are then added with stirring to 200 grams of mixture containing 4% aqueous sodium hypochlorite and 4% aqueous lithium hypochlorite. Sufficient 2M aqueous NaOH is added to bring the pH of the solutions to 13.4. The mixtures are then heated to 110° F. and maintained at that temperature with stirring for a period of two weeks. The resulting solutions remain clear as a single phase when used as laundry bleaches. The resulting bleached laundry batches on dry-out in an atmosphere of 50% relative humidity retain aromas as set forth in Table I of Example III supra whereas without the use of the perfume substances of Table I of Example III supra, the bleached laundry batches have faint, characteristic disagreeable "hypochlorite" aromas.

EXAMPLE XIV

Four drops of each of the substances of Table I of Example III supra are added to 1.5 grams of Aromox ® NCMDW to produce a clear premix. The clear premixes are added to 200 grams in each case of CLOROX ® with stirring resulting in a clear single phase solution. Sufficient 1M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic hypochlorite aroma but does have a faint pleasant aroma as set forth in Table I of Example III supra. Furthermore, no such characteristic "hypochlorite" aroma is retained on the hands of the individual handling such laundry in both the wet and the dry states.

EXAMPLE XV

Four drops of each of the substances of Table I of Example III supra are added to 1 gram of n-undecyl dimethyl amine oxide to produce a clear premix in each case. The clear premix is added to 200 grams of CLOROX ® with stirring resulting in a clear, single phase solution. Sufficient 1M aqueous NaOH is added to bring the pH of the mixture to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic hypochlorite odor but does have a faint pleasant odor as set forth in Table I of Example III supra. Furthermore, no such characteristic "hypochlorite" odor is retained on the hands of the individual handling such laundry in both the wet and the dry states.

EXAMPLE XVI

Four drops of each of the substances of Table I of Example III supra is added to 1 gram of n-dodecyl dimethyl amine oxide to produce a clear premix. The clear premix is added to 200 grams of CLOROX ® with stirring resulting in a clear stable single phase solution. Sufficient 1M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant aroma as set forth in Table I of Example III supra. Furthermore, no such characteristic "hypochlorite" aroma is retained on the hands of the individual handling such laundry in both the wet and the dry states.

EXAMPLE XVII

One gram of n-tridecyl dimethyl amine oxide is admixed with eight drops of each of the substances of Table I of Example III supra. Each of the premixes is then, with stirring, added to 200 grams of a 7% aqueous solution of lithium hypochlorite. Sufficient 3M aqueous LiOH is added to bring the pH of the solution to 13.4. The mixture is then heated to 120° F. and maintained at that temperature with stirring for a period of one week. The resulting solution remains clear in a single phase. When used as a laundry bleach, the resulting bleached laundry on dry-out in an atmosphere of 50% relative humidity retains an aroma as set forth in Table I of Example III supra; whereas without the use of any of the substances of Table I of Example III supra, the bleached laundry has a faint, characteristic, disagreeable "hypochlorite" aroma.

What is claimed is:

1. The compound defined according to the structure:

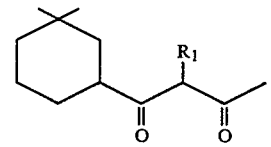

wherein $R_1$ is selected from the group consisting of hydrogen and 2-propenyl.

2. The compound of claim 1 wherein $R_1$ is hydrogen.
3. The compound of claim 1 wherein R is 2-propenyl.

* * * * *